United States Patent [19]

Shuster

[11] Patent Number: 4,553,677
[45] Date of Patent: Nov. 19, 1985

[54] DILUTION BOTTLE

[75] Inventor: Herbert V. Shuster, Waban, Mass.

[73] Assignee: Aseptic Technologies, Inc., Quincy, Mass.

[21] Appl. No.: 618,832

[22] Filed: Jun. 8, 1984

[51] Int. Cl.[4] ............................................... B65D 1/02
[52] U.S. Cl. .................................... 215/33; 215/1 C; 366/130
[58] Field of Search ..................... 366/130; 215/32, 33, 215/34, 250, 257

[56] References Cited

U.S. PATENT DOCUMENTS

| 45,309 | 12/1864 | Bliss | 366/130 |
| 2,372,181 | 3/1945 | Barr | 215/33 |
| 4,113,129 | 9/1978 | Cambio | 215/32 X |
| 4,444,307 | 4/1984 | Jermyn | 366/130 X |
| 4,478,342 | 10/1984 | Slater et al. | 215/32 |

FOREIGN PATENT DOCUMENTS

| 7869 | 2/1980 | European Pat. Off. | 215/257 |
| 2017661 | 10/1979 | United Kingdom | 215/257 |

Primary Examiner—Donald F. Norton
Attorney, Agent, or Firm—Schiller & Pandiscio

[57] ABSTRACT

A dilution bottle for mixing a sample material with a sterile diluent solution. The bottle comprises side wall portions of synthetic polymeric material formed around the central axis of the bottle, a bottom wall of polymeric material closing off one end of the bottle, and the opposite end of the bottle including an opening. At least one side wall portion of the bottle is formed with one or more concave protrusions extending into the interior of the bottle, the protrusions being dimensioned so as not to obstruct the introduction of insertion means along said axis. The bottle also includes means for sealing the opening of the bottle so as to maintain aseptic conditions within the bottle.

7 Claims, 4 Drawing Figures

DILUTION BOTTLE

The present invention relates to dilution bottles, and more particularly, to an improved, relatively inexpensive, disposable dilution bottle intended to be formed, filled and sealed aseptically in one sequence of operations, the bottle being formed to provide means integral therewith for facilitating the dispersement of a sample throughout a diluent solution.

Dilution bottles are widely used in microbiological laboratories in the food, pharmaceutical, chemical, medical fields and similar industries to mix a sample with a sterile diluent solution. A typical prior art dilution bottle is made of glass and has side wall portions, a flat bottom wall and an upper reduced neck providing an opening opposite the bottom wall. The bottle may be of circular, square or other cross-section. The bottle is usually provided with one or more fiducial markings on a side wall portion for indicating particular fill levels so that a proper amount of diluent solution, often an aqueous buffer, can be provided in the bottle and sterilized before adding a precise amount of sample material to the diluent solution. Such bottles are often sealed typically with a conventional screw-cap or an Escher type stopper having an elongated rubber conical portion extending well down into the bottle when the stopper is in place.

In use, the dilution bottle is usually filled with a diluent solution to a fiducial mark or slightly above. The conical portion of the Escher stopper is loosely inserted in the opening of the bottle to permit venting of expanding gas from the interior of the bottle during subsequent sterilization. The bottle and stopper are then placed and heated in an autoclave so that the contents of the bottle are sterilized. Following sterilization, as the bottle cools, the conical portion of the stopper is drawn more tightly in the opening of the bottle insuring that the contents of the bottle remain sterile.

Sample material to be tested, may then be added by removing the stopper, flaming the opening, inserting a sterile pipet to inject a precise amount of the sample material into the bottle, reflaming the opening and reinserting the stopper. The sample may be completely soluble in the diluent and therefore readily dispersed uniformly. Alternatively, the mixture may require substantial agitation to disperse the sample throughout the diluent solution.

Because prior art bottles are usually made of glass and utilize Escher stoppers, they are expensive and, therefore, are reused. Used bottles, accordingly, must be thoroughly cleaned before reuse. Depending upon the prior use of the bottle and stopper, used bottles may be difficult to clean, and therefore, add time and expense to the employment of such bottles.

It is an object of the present invention to provide an improved dilution bottle which substantially overcomes or reduces the above-noted problems of the prior art.

Another object of the present invention is to provide an improved dilution bottle which can be easily formed and filled aseptically in one manufacturing operation.

And another object of the present invention is to provide an improved dilution bottle inexpensive to manufacture and disposable after use.

Yet another object of the present invention is to provide an improved dilution bottle constructed to facilitate the dispersement of the sample material through the diluent material when the bottle is shaken.

These and other objects are achieved by an improved dilution bottle for making mixture of a sample material and a sterile diluent solution. The bottle comprises side wall portions of synthetic polymeric material formed around the central axis of the bottle, a bottom wall of the polymeric material closing off one end of the bottle, and the opposite end of the bottle including an opening. At least one side wall portion of the bottle is formed as a concave protrusion extending into the interior of the bottle, the protrusion being dimensioned so as not to obstruct the introduction of insertion means along the axis. The bottle also includes means sealing the opening thereof so as to maintain aseptic conditions therein.

Other objects of the invention will in part be obvious and will in part appear hereinafter. The invention, accordingly, comprises the product possessing the features, properties and relation of components which are exemplified in the following detailed disclosure, and the scope of the application of which will be indicated in the claims.

For a fuller understanding of the nature and objects of the present invention, reference should be had to the following detailed description taken in connection with the accompanying drawing, wherein.

Figure 1:
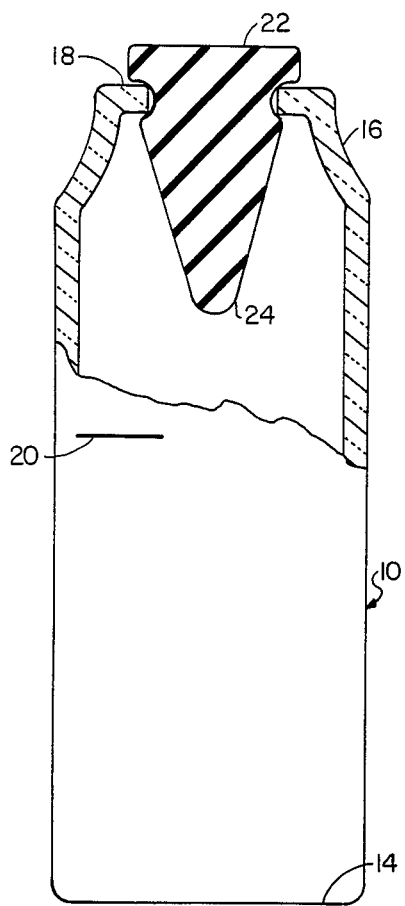
FIG. 1 is a longitudinal view in cross-section of a dilution bottle of the prior art type.

In FIG. 1 there is shown a glass dilution bottle 10 typical of the prior art. Bottle 10 has side walls 12, flat bottom wall 14 and neck 16 narrowed at the top to form opening 18. One side wall 12 is typically provided with one or more fiducial markings 20 for indicating the fill level of the diluent solution placed in the bottle. For example, where the bottle is used to contain a diluted material with a ratio 1:99 of sample material to diluent, fiducial marking 20 might indicate 99 ml. of aqueous buffer solution so that the addition of one ml. of sample material would provide a 1:100 dilution. Escher stopper 22, including characteristic conical portion 24 intended to extend along the central long axis of bottle 10, is provided for sealing opening 18. Bottle 10 can be made in accordance with any of the techniques well-known in the glass-forming art. After the bottle is made, a diluent solution, typically an aqueous phosphate buffer, or an aqueous 0.1% peptone solution, is poured into the bottle so as to result in a post-sterilization level at fiducial mark 20. Stopper 22 is loosely placed in the opening 18 to permit venting of escaping gas from the interior of the bottle during subsequent sterilization, and the bottle with emplaced stopper 22 are disposed in a system, such as an autoclave, for sterilizing the bottle and its contents. As the bottle is heated, gas within the bottle expands. Conical portion 24 of stopper 22 provides a large surface area so that the stopper is lifted by the heated gas which tends to escape around the edge of opening 18. Once sterilization is completed, the bottle is allowed to cool, and the contracting gas within the bottle pulls the Escher stopper tightly into opening 18 to provide a seal, thereby preserving sterile conditions within the bottle.

When it is desired to mix sample material with the diluent solution, the stopper is removed and opening 18 is flamed to assure sterility of the periphery of the neck. Means, such as a pipette, for transferring a precise amount of sample material, is then inserted through opening 18 and desired sample material added to the diluent material. Opening 18 is reflamed and stopper 22 reinserted.

It is evident that the several separate and unrelated operations required to manufacture glass bottles 10, manufacture screw-caps or Escher stoppers 18, add the diluent solution to the bottle, insert the stoppers into the bottles, sterilize the contents and later clean the bottles after use, is a costly and time consuming process.

The bottle of the present invention is preferably made of a thermoplastic, synthetic polymer on state-of-the-art blow molding machinery in such a manner that the bottle-forming step, diluent-filling step of a sterile diluent under aseptic conditions, and sealing step are all carried out in one unbroken sequence of operations. Importantly, the bottle of the present invention is formed with a side wall having at least one concave protrusion or projection extending laterally into the bottle, for aiding dispersion and/or mixing and breaking up any clumping of the sample material as the bottle is shaken with the sterile diluent and later added sample material.

Figure 2:
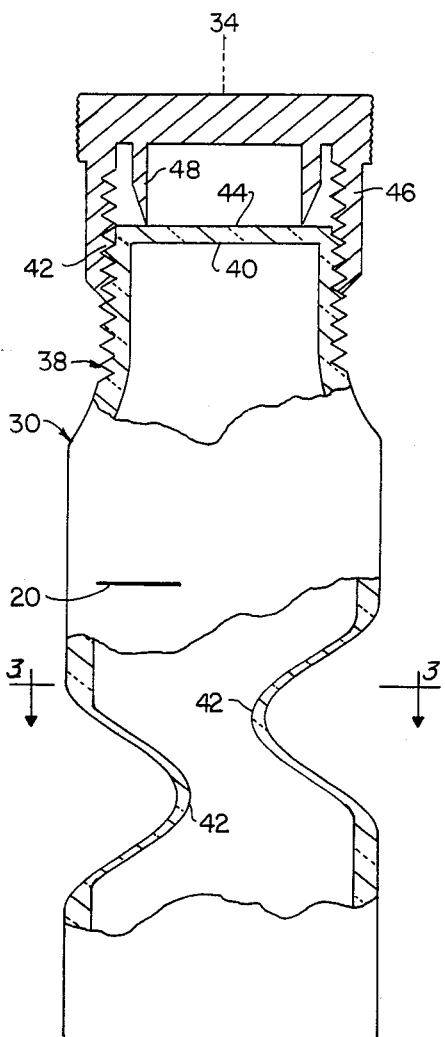
FIG. 2 is a longitudinal view, partly in cross-section and partly broken away, showing one embodiment of the present invention.
Figure 3:
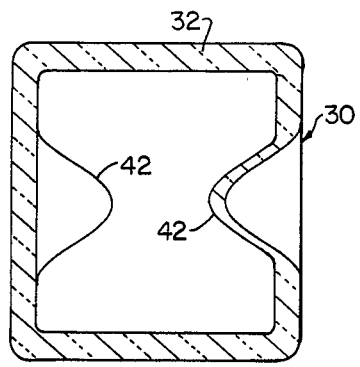
FIG. 3 is a cross-sectional view taken along line 3—3 in FIG. 2.

More particularly, referring to FIGS. 2 and 3, the preferred bottle 30 is formed to have side wall portions 32 extending about a central longitudinal axis 34 of the bottle, flat bottom wall 36 and an upper neck 38 initially having opening 40 therein disposed about axis 34. The cross-sectional shape of bottle 30 taken along line 3—3 in FIG. 2 can take any form, such as the substantially square shape shown, circular, eliptical, etc.

At least one, and preferably two side wall portions 32 are each formed so as to constitute concave conical protrusions or projections 42 extending laterally into the interior of bottle 30. Such projections serve to aid in breaking up, if necessary, a sample material added later to diluent solution in the bottle so as to faciltate dispersement of the sample material throughout the diluent. The thickness of the wall forming each concave conical protrusion 42 is substantially uniform and is somewhat thinner than the thickness of the remainder of wall 32. In a preferred embodiment, the two protrusions 42 are diametrically opposed to one another and are axially offset from one another along axis 34. It is preferred that the apices of protrusions 42 be spaced sufficiently from axis 34 so that a pipette or other simple sample transfer device can be ultimately inserted along axis 34 into the bottle without being impeded by protrusions 42. In a preferred form of the bottle of the invention, each protrusion 42 has a height (measured from the base of the protrusion to its apex) approximately equal to its base or spacing diameter. While the number of protrusions 42 is not critical, two are preferred, and although protrusions 42 can be formed in other conical-like geometric shapes, such as a frustoconical or pyramidal shape, the conical configuration shown has proven to be preferred, since it is most easily formed during molding and is effective in breaking up clumping of a sample to facilitate dispersement of that sample throughout the diluent solution.

The bottle is preferably made of a synthetic polymer, typically a thermoplastic or blow-moldable material, such as polypropylene or polyethylene, so that the bottle can easily be mass-produced by blow molding. The preferred method of making the dilution bottle of the present invention is by using a blow-fill-seal machine, preferably with indexing and encapsulation of an ancillary closure. Such blow-fill sealing equipment is typically that described in U.S. Pat. Re No. 27,155 issued July 20, 1971 to G. Hansen, and is commercially available from Automatic Liquid Packaging, Inc. of Elk Grove, Ill.

In operation of such equipment, a thermoplastic or blow-moldable material such as polyethylene is continuously extruded in a tubular shape or parison in a high temperature (e.g. ca. 400° F.) sterile environment within a molding cavity in a double split bottle mold. Typically, for commercial production, the mold should be a multiple cavity mold into which several parisons may be simultaneously extruded. After each parison has been extruded to a proper length, the bottom portion of the split mold is closed, pinching off the bottom of each parison, while the top of each parison is held in place by a set of holding jaws. The mold is then transferred to a position under a blowing and filling means or nozzles. The latter are lowered into each parison until they form a seal with the neck of the mold. The bottles are then formed by blowing compressed air through the nozzles into that portion of each parison that is within the bottom mold cavity.

Following formation of the bottle, the compressed air within the mold is vented, and a metered amount of the sterile diluent solution is injected into the bottles through the blow-fill nozzles. Following injection of the predetermined amount of solution into the bottles, the nozzles are retracted from the upper portion of the parisons. At this point in the cycle the portion of the parisons between the top of the bottom portion of the mold and the holding jaws are still semi-molten. Separate sealing jaws or an upper portion of the double split mold are then closed to pinch off the top of each parison and form a seal. After each of the heads is sealed, both portions of the mold are opened and the finished bottles, completely formed, filled and sealed, and often fully deflashed, are then taken from the machine.

Many different forms of closures can be employed depending upon mold configuration and variations of the machine used to form the bottles of the present invention. For example, as shown in the embodiment of FIG. 2, the closure can be made in the form of a simple film or disk 44 of plastic. In such case, the mold for bottle 30 preferably is formed so that during the molding operation the exterior surface of of neck 38 adjacent opening 40 is configured with a helical thread 42. This thread permits bottle cap 46 to be screwed later around neck 38. In such case, cap 46 is preferably of a known type which includes a sharp-edged circular cutter or punch 48 which extends inside the cap downwardly toward disc 44 when the cap is partially screwed onto thread 42.

In use of the bottle of FIG. 3, a suitable cutting cap screwed over neck 38 is tightened until punch 48 cuts through disc 44, exposing the interior of the bottle. The cap is removed with the cut disc held tightly within the cap, the sample material is inserted as with a pipette, opening 38 and the cap both may be flamed, and the cap is screwed back onto the bottle. The concave protrusions 42 formed by the wall portions of bottle provide means for breaking up samples and aiding their dispersement throughout the diluent solution previously disposed in the bottle.

Figure 4:
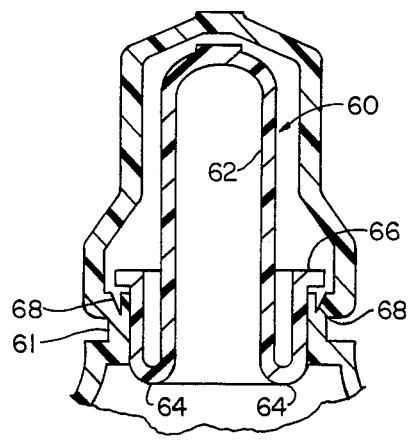
FIG. 4 is a fragmentary longitudinal view, partly in cross section, of a preferred form of closure of the bottle of the present invention.

In the preferred embodiment shown in FIG. 4, the bottle closure is formed so that no flaming of the bottle opening is needed during use. To this end, the blow-fill-sealing equipment includes one or any of the several known automatic indexing devices presently commercially available. These indexing devices serve to introduce an ancillary part or closure 60 into neck 61 of bottle 30 immediately following the operation which fills the bottle with the diluent solution. Closure 60 is a pre-sterilized, liquid-impermeable member, typically formed of a resilient material such as plastic, thin metal, rubber or the like. Closure 60 includes a cylindrical, closed, center cap 62 formed integrally with and coaxially surrounded at one end thereof by hemi-torus 64, i.e. a shape that would be approximated by cutting a hollow torus in substantially equal parts along a plane perpendicular to the axis of revolution of the torus. The periphery of hemi-torus 64 in turn is coaxially surrounded by lip 66 formed integrally with and extending outwardly from the hemi-torus as a flat ring. The axial height of cap 62 is much longer than the axial height of hemitorus 64 to provide a manually engageable handle. The external diameter of hemi-torus 64 is slightly greater than the interior diameter of neck 61 of bottle 30, so that when closure 60 in inserted by the indexing mechanism, the exterior periphery of hemitorus 64 is compressed resiliently inwardly to form a tight friction fit. Lip 66 serves to engage the upper end of neck 61, thereby limiting the extent to which closure 60 can be inserted into neck 61.

After insertion of closure 60 into neck 61, the indexing mechanism is withdrawn and the separate sealing jaws or secondary mold are closed to pinch the still moldable parison top at a point slightly above the location of the top of closure 60, and thus seal and encapsulate the latter. Preferably, the separate sealing jaws are configured to provide a frangible peripheral web in the seal, by forming circular groove 68 at the base of the seal, along which groove a fracture line can easily be created by simply twisting the seal, all as described in U.S. Pat. No. 3,597,793 to Weiler et al.

In use of the bottle of FIG. 4, one simply need apply mechanical force such as a twist to the cap, causing the latter to fracture along groove 68. The cap can then be readily removed, exposing the top of bottle 30 sealed with sterile closure 60. The latter can easily be removed by finger pressure sufficient to overcome the friction fit of the stopper in the bottle neck.

One need not disc-seal bottle 30, but instead, provided that the operation takes place immediately after filling the bottle with sterile diluent, opening 40 may be sealed in other suitable ways, such as with a pre-sterilized screw cap or the like. Such closures, however, are not particularly desirable for manufacturing speed, maintenance of aseptic conditions, or cost.

Sealed bottle 30 thus provides an improved product for containing a premeasured sterile diluent solution ready for mixture with a sample material. Bottle 30 can be easily formed, filled with sterile diluent solution and sealed while maintaining aseptic conditions, all in one manufacturing operation. Finally, because the bottle is made of inexpensive plastic, it can be disposed of after use, avoiding the necessity of cleaning the bottles as encountered with the prior art glass bottles, such as that shown in FIG. 1.

Since certain changes may be made in the above products without departing from the scope of the invention herein involved, it is intended that all matter contained in the above description or shown in the accompanying drawing shall be interpreted in an illustrative and not in a limiting sense.

What is claimed is:

1. A dilution bottle for mixing sample material with a sterile diluent solution, said bottle comprising, in combination:

side wall portions of blow-moldable, synthetic polymeric material formed around the longitudinal axis of said bottle, a bottom wall of said polymeric material closing off one end of said bottle, and the opposite end of said bottle including an opening, at least one side wall portion of said bottle being formed with a protrusion extending into the interior of said bottle; and means for sealing said opening of said bottle so as to maintain aseptic conditions within said bottle, said means for sealing said bottle comprising an ancillary sterile stopper emplaced in said opening, and a seal formed of said plastic material integrally with said bottle and spaced from and encapsulating said stopper, said stopper being shaped as an extended closed cylinder surrounded coaxially at one end thereof by a hemi-torus which in turn is surrounded coaxially by a disc-shaped rim, said cylinder, hemi-torus and rim being formed integrally of a resilient, liquid-impermeable material.

2. A bottle according to claim 1, wherein said protrusion is conical-like in shape.

3. A bottle according to claim 2, wherein said bottle includes at least two of said protrusions formed as integral parts of diametrically-opposed side portions of said bottle.

4. A bottle according to claim 3, wherein said protrusions are axially-offset from one another with respect to said longitudinal axis.

5. A bottle according to claim 3, wherein the apices of said protrusions are spaced from said central axis so as not to obstruct the introduction of insertion means along said axis.

6. A bottle according to claim 1, wherein said seal includes a groove positioned so that said seal, upon the application of mechanical force thereto, will fracture to provide access to said stopper.

7. A bottle according to claim 1, wherein a side wall portion of said bottle includes at least one fiducial mark for indicating a fill level for said sterile diluent solution.

* * * * *